United States Patent [19]

Picha

[11] Patent Number: 5,057,118
[45] Date of Patent: Oct. 15, 1991

[54] VESSEL OCCLUSION DEVICE

[75] Inventor: George J. Picha, Independence, Ohio

[73] Assignee: Applied Medical Technology, Inc., Independence, Ohio

[21] Appl. No.: 529,375

[22] Filed: May 29, 1990

[51] Int. Cl.$^5$ .............................................. A61B 17/00
[52] U.S. Cl. ..................................... 606/158; 606/157
[58] Field of Search ............... 606/157, 151, 139, 158, 606/203; 128/831, 843, DIG. 26

[56] References Cited

U.S. PATENT DOCUMENTS

| 3,667,471 | 6/1972 | Doty et al. | 606/158 |
| 3,880,166 | 4/1975 | Fogarty | 606/158 |
| 3,993,076 | 11/1976 | Fogarty | 606/158 |
| 4,390,019 | 6/1983 | LeVeen et al. | 606/158 |
| 4,611,593 | 6/1986 | Fogarty et al. | 606/158 |
| 4,813,416 | 3/1989 | Pollak et al. | 606/151 |

Primary Examiner—Stephen C. Pellegrino
Assistant Examiner—Gary Jackson
Attorney, Agent, or Firm—Pearne, Gordon, McCoy & Granger

[57] ABSTRACT

A vessel occlusion device has a base with a generally flat surface against which a vessel may be positioned. One end of a strap is fastened to the base. The other end of the strap is adapted to be removably attached to the base with the vessel between the base and the strap. The strap is provided with a plurality of attachment holes for selectively attaching the end of the strap to the base at any one of a plurality of adjustable positions. The vessel occlusion device provides a traumatic occlusion with multiple vessel occlusion adjustments.

10 Claims, 1 Drawing Sheet

VESSEL OCCLUSION DEVICE

BACKGROUND OF THE INVENTION

1. Field of the Invention

This invention relates to microsurgery and vascular surgery, and more particularly to vessel occluding instruments for use in anastomosis.

2. Description of the Prior Art

In microsurgical procedures, such as vessel anastomosis, routine occlusion of vessels is accomplished by various vessel occlusion instruments. Conventional clip and clamp-type vessel occlusion instruments have been used for many years, but the use of these conventional vessel occlusion instruments is often undesirable due to the anatomy and location of the vessels as well as the fragile nature of the vessels. Conventional clip and clamp-type vessel occlusion instruments often traumatize the vessel and bruise the tissue. This trauma complicates the recovery of the vessel following the anastomosis.

Various other types of vessel clamping or occlusion devices have been proposed.

British Patent No. 972,731, issued Oct. 14, 1964, to Gerendas, shows an artery clamp having a semi-rigid base with a pair of outwardly extending clamping prongs. The vessel is positioned against the base, and a matching plate with openings is placed over the vessel. The upper plate is pressed over the prongs to clamp the plates together with the vessel between the plates. Alternatively, the Gerendas patent provides a clamping member which extends over the base and has prongs at each end to engage openings in the base. There is no adjustability in the positioning of the clamping device, so that a single device will provide less clamping force on smaller vessels. In addition, these types of clamping devices are difficult to remove without traumatizing the vessel.

U.S. Pat. No. 3,993,076, issued to Fogarty, shows another vessel occluding instrument with a semi-rigid body member with a resilient pad attached to the body member. The vessel is positioned against the pad. The body has a hole at one end and a slot at the opposite end. A length of surgical tape is secured at one end in the hole in the body member and positioned around the vessel so that the vessel is positioned between the pad and the tape. The end of the tape is then pulled into the slot to tightly secure it to the body member in a manner that applies sufficient pressure to close the vessel. While this device provides a selective clamping pressure to the vessel, it appears that it would difficult to use this device for atraumatic occlusion since the risk of some trauma to the affective area is likely, particularly during removal. In addition, it would be relatively difficult to secure the end of the tape in the slot in a secure manner such that the tape would not slip and reduce clamping pressure to the vessel.

U.S. Pat. No. 3,880,166, issued to Fogarty shows a similar device in which the surgical tape is formed in a double loop with one loop replacing the pad in the previous Fogarty patent. Here again, the device would be difficult to apply and remove without the risk of trauma.

Various other medical clamping devices are shown in other patents, particularly U.S. Pat. No. 3,204,636, issued to Kariher et al.; and U.S. Pat. No. 3,910,280, issued to Talonn. Other devices of interest are shown in the following patents: U.S. Pat. No. 1,607,996, issued to Morgenthaler; U.S. Pat. No. 3,576,054, issued to Rynk; and U.S. Pat. No. 3,699,957 issued to Robinson.

SUMMARY OF THE INVENTION

The disadvantages of the prior art clamping devices are overcome by the present invention of a vessel occlusion device which provides atraumatic occlusion with multiple vessel occlusion adjustments.

The vessel occlusion device of the present invention provides a base against which the vessel may be positioned and utilizes a strap of soft foam to extend over the vessel against the base to clamp the vessel and provide atraumatic occlusion. The strap is preferably formed of a soft foam material to provide absorbency and to keep the vessel moist during anastomosis. The strap has on it a plurality of attachment means for attaching the free end of the strap to the base to clamp the vessel with the desired amount of clamping force. A variety of vessel occlusion adjustments are thus provided and unnecessary clamping pressure is avoided.

The vessel occluding device of the present invention is also provided with means for assisting in handling and placing the device. A tab is provided at one end of the base, and the tab is connected to the base by a narrow neck providing a pair of slots into which a pickup instrument can be inserted to hold the device stably in the vessel field.

By using soft materials throughout the vessel occlusion device of the present invention, trauma to the vessel is reduced and recovery of the vessel following an anastomosis procedure is enhanced.

These and other advantages are provide by the present invention of a vessel occlusion device which comprises a base and a strap. The base has a generally flat surface against which a vessel may be positioned. The strap has two ends. One end of the strap is fastened to the base. The other end of the strap is adapted to be removably attached to the base with the vessel between the base and the strap. The strap is provided with a plurality of attachment means for selectively attaching said other end of the strap to the base at any one of a plurality of adjustable positions.

DETAILED DESCRIPTION OF THE PREFERRED EMBODIMENT

Figure 1:
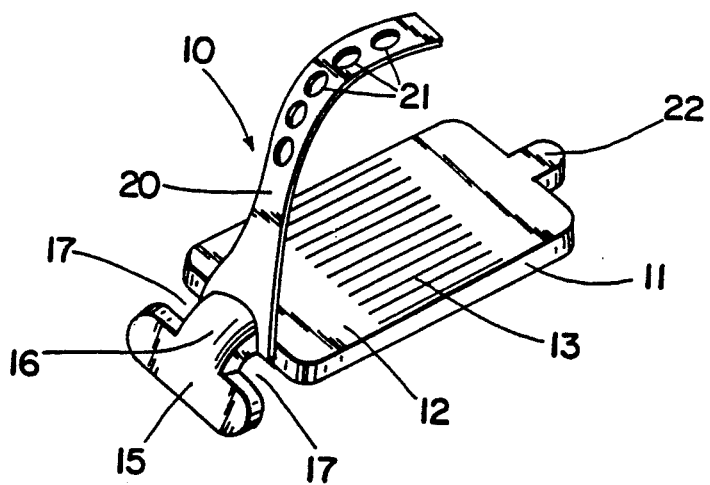
FIG. 1 is a perspective view of the vessel occlusion device of the present invention prior to use.

Referring more particularly to the drawings, and initially to FIG. 1, there is shown the vessel occlusion device 10 of the present invention. The device 10 comprises a flat base 11 formed of a suitable plastic material and preferably colored blue so that it contrasts with the colors of the surgical field and is more easily identifiable during the surgical procedure. The base 11 provides a bed 12 for placement of a vessel. The bed 12 may be approximately between 1 mm and 4 mm in width, depending upon the size of the vessel being occluded. The surface of the base 11 providing the bed 12 is preferably provided with a plurality of serrations 13 to provide texture to the surface and prevent slippage of the vessel.

Figure 2:
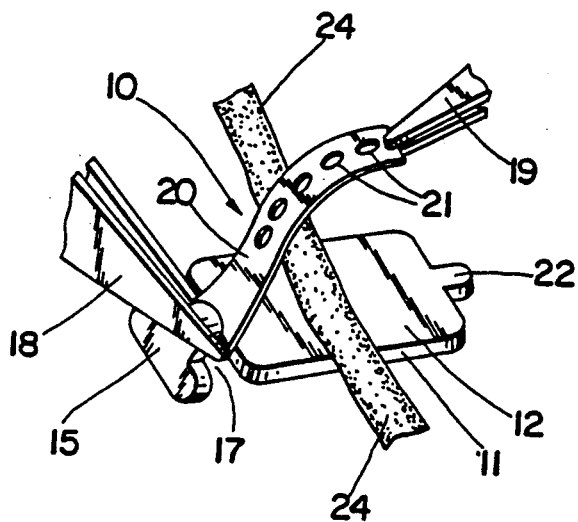
FIG. 2 is a perspective view of the device of FIG. 1 positioned for use in vessel occlusion.
Figure 3:
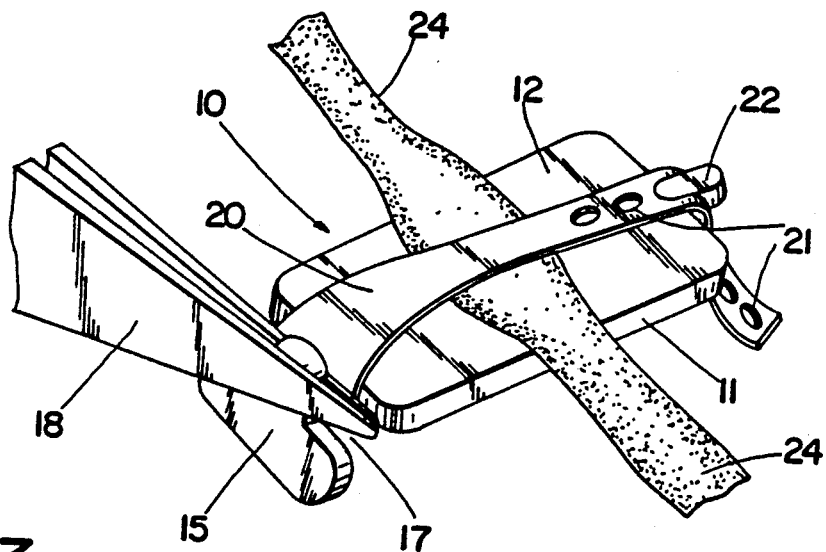
FIG. 3 is a perspective view of the device of FIGS. 1 and 2 used for vessel occlusion.

A tab 15 is integrally formed at one end of the base 11 to provide a means for holding the device 10. The tab 15 preferably extends at an angle of approximately 45° with respect to the base 11 so that the device 10 can be easily held at the proper angle in the field. The tab 15 is connected to the base 11 by a narrow neck 16 so that slots 17 are provided between the tab 15 and the base 11 for the placement of an instrument 18 (as shown in FIGS. 2 and 3). The location of the slots 17 and the angle of the tab 15 allow the device 10 to be picked up and precisely held in a stable position in the vessel field. It is important that the neck 16 be sufficiently thin to allow the device to be stably held in position during the clamping. In addition, the angle of 45° between the tab 15 and the base 11 is important so that the device is held at the proper angle to approach the field properly.

A strap 20 is attached at one end to the neck 16. The strap 20 is preferably made of silicone or polyurethane foam to provide a soft material for occluding the vessel, to provide enhanced friction to limit migration of the device during vessel occlusion, and to provide absorbency to keep the vessel moist during anastomosis. The other end or free end of the strap 20 is provided with a plurality of holes 21 spaced apart along the strap. Each of the holes 21 is sized so that it fits over a projection 22 extending from the end of the base 11 opposite the tab 15. Each of the holes 21 thus provides a means for attaching the free end of the strap 20 to the projection 22. Because a plurality of holes 21 are provided, a strap 20 may be selectively attached to the base 11 at any one of various positions depending upon the size of the vessel and the desired clamping pressure, so that multiple occlusion adjustments are possible and unnecessary clamping pressure is eliminated. The holes 21 should be as close together as possible without affecting the strength of the strap 20 so that the large range of adjustments are provided and no greater clamping pressure is applied to the vessel than is necessary to achieve occlusion.

The use of the vessel occlusion device 10 of the present invention is shown in FIGS. 2 and 3. The surgeon places the device 10 in the desired position in the field by gripping the device with an instrument 18 placed in the slots 17 between the tab 15 and the base 11. The base 11 of the device is slipped beneath a vessel 24 to be occluded so that the vessel rests on the bed 12. The surgeon then grasps the free end of the strap 20 with another instrument 19 and positions the strap across the vessel as shown in FIG. 2. The surgeon pulls the end of the strap 20 across the vessel 24 more tightly until the desired vessel occlusion is achieved. The proper clamping pressure is thus determined. The appropriate hole 21 in the strap 20 is then ascertained depending upon the desired clamping pressure, and this hole is positioned over the projection 22 as depicted in FIG. 3. The vessel 24 is inspected to determine that flow has stopped and to determine that the occlusion has occurred in the desired location. At this point the vessel occlusion is completed, and the surgical procedure can be performed. The foam material of the strap 20 provides desired frictional engagement of the vessel 24 so that migration of the device 10 during the surgical procedure is minimized.

At the completion of the surgical procedure, the occlusion device 10 is removed. The strap 20 is grasped by an instrument 19 and detached from the projection 22 with the device 10 held by another instrument 18 at the slots 17. The device 10 is carefully removed from around the vessel 24 using the instrument 18, and the entire device is discarded. It has been found that the careful removal of the device 10 in this manner is possible, and that the device of the present invention does not have to be cut off as was the case with many occluders of the prior art. This permits the device of the present invention to be used with a significant decrease in trauma to the vessel.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way this is inconsistent with the extent to which the progress in the art has been advance by the invention.

What is claimed is:

1. A vessel occlusion device comprising:
    a base having a generally flat surface against which a vessel may be positioned; and
    a strap formed of a soft absorbant material, the strap having two ends, one end being fastened to the base, the other end adapted to be removably attached to the base with the vessel between the base and the strap, at least one of the ends extending beyond the base, the strap provided with a plurality of attachment means for selectively attaching said other end of the strap to the base at any one of a plurality of adjustable positions.

2. A vessel occlusion device as defined in claim 1, comprising in addition placement means extending from the base for engagement by an instrument to stably hold the device in the vessel field.

3. A vessel occlusion device as defined in claim 2, wherein the placement means comprises a tab extending from the base.

4. A vessel occlusion device as defined in claim 1, wherein the surface of the base has serrations to provide texture.

5. A vessel occlusion device as defined in claim 1, wherein the strap is made of a soft foam material.

6. A vessel occlusion device as defined in claim 1, wherein the attachment means comprises a plurality of holes longitudinally spaced in the strap, each of the holes adapted to engage a projection on the base.

7. A vessel occlusion device, comprising:
    a base having a generally flat surface against which a vessel may be positioned;
    a strap having two ends, one end being fastened to the base, the other end adapted to be removably attached to the base with the vessel between the base and the strap, the strap provided with a plurality of attachment means for selectively attaching said other end of the strap to the base at any one of a plurality of adjustable positions; and
    a tab extending from the base for engagement by an instrument to stably hold the device in the vessel field, the tab being connected to the base by a neck which provides slots between the tab and the base for engagement by the instrument.

8. A vessel occlusion device as defined in claim 7 wherein the end of the strap is attached to the neck.

9. A vessel occlusion device, comprising:

a base having a generally flat surface against which a vessel may be positioned;

a strap having two ends, one end being fastened to the base, the other end adapted to be removably attached to the base with the vessel between the base and the strap, the strap provided with a plurality of attachment means for selectively attaching said other end of the strap to the base at any one of a plurality of adjustable positions; and a tab extending from the base for engagement by an instrument to stably hold the device in the vessel field, the end of the strap being attached to the base at the location of the tab.

10. A vessel occlusion device comprising:

a base having a generally flat surface against which a vessel may be positioned, the surface of the base having serrations to provide texture, the base having a projection extending from one end thereof; and a strap made of a soft foam material and having two ends, one end being fastened to the base, the other end adapted to be removably attached to the base with the vessel between the base and the strap, the strap provided with a plurality of attachment means for selectively attaching said other end of the strap to the base at any one of a plurality of adjustable positions, the plurality of attachment means comprising a plurality of holes longitudinally spaced in the strap, each of the holes adapted to engage the projection on the base; and placement means extending from the base for engagement by an instrument to stably hold the device in the vessel field, the placement means comprising a tab extending from the end of the base opposite the projection, the tab connected to the base by a neck which provides slots between the tab and the base for engagement by the instrument, said one end of the strap being attached to the base at the neck.

* * * * *